(12) United States Patent
Buelo et al.

(10) Patent No.: US 8,911,712 B2
(45) Date of Patent: Dec. 16, 2014

(54) MULTI-PURPOSED DENTIFRICE

(75) Inventors: Adonis Buelo, Leonardo, NJ (US); Anthony Cirigliano, Langhorne, NJ (US); Elizabeth Major, Jacobstown, NJ (US); Yun Xu, Langhorne, PA (US)

(73) Assignee: Church & Dwight, Co., Inc., Princeton, NJ (US)

( * ) Notice: Subject to any disclaimer, the term of this patent is extended or adjusted under 35 U.S.C. 154(b) by 0 days.

(21) Appl. No.: 13/877,385

(22) PCT Filed: Oct. 3, 2011

(86) PCT No.: PCT/US2011/054547
§ 371 (c)(1),
(2), (4) Date: Apr. 2, 2013

(87) PCT Pub. No.: WO2012/047781
PCT Pub. Date: Apr. 12, 2012

(65) Prior Publication Data
US 2013/0189201 A1 Jul. 25, 2013

Related U.S. Application Data

(60) Provisional application No. 61/389,400, filed on Oct. 4, 2010.

(51) Int. Cl.
*A61K 8/24* (2006.01)
*A61Q 11/00* (2006.01)
*A61K 8/19* (2006.01)
*A61K 8/22* (2006.01)
*A61K 8/86* (2006.01)
*A61K 8/20* (2006.01)

(52) U.S. Cl.
CPC ... *A61K 8/24* (2013.01); *A61K 8/19* (2013.01); *A61K 8/86* (2013.01); *A61K 8/22* (2013.01); *A61Q 11/00* (2013.01); *A61K 8/20* (2013.01); *A61K 2800/31* (2013.01)
USPC .................. 424/53; 424/49; 424/56; 424/57; 424/401

(58) Field of Classification Search
CPC ....................................................... A61K 8/19
USPC ........................................................... 424/53
See application file for complete search history.

(56) References Cited

U.S. PATENT DOCUMENTS

| | | | |
|---|---|---|---|
| 3,376,110 A | | 4/1968 | Shiraeff |
| 3,480,557 A | | 11/1969 | Shiraeff |
| 4,891,211 A | | 1/1990 | Winston |
| 4,897,258 A | * | 1/1990 | Rudy et al. ...................... 424/53 |
| 4,971,782 A | | 11/1990 | Rudy et al. |
| 5,037,639 A | | 8/1991 | Tung |
| 5,085,853 A | | 2/1992 | Williams et al. |
| 5,122,370 A | | 6/1992 | Merianos et al. |
| 5,268,167 A | | 12/1993 | Tung |
| 5,427,768 A | | 6/1995 | Tung |
| 5,437,857 A | | 8/1995 | Tung |
| 5,455,024 A | | 10/1995 | Winston et al. |
| 5,460,803 A | | 10/1995 | Tung |
| 5,571,502 A | | 11/1996 | Winston et al. |
| 5,614,147 A | | 3/1997 | Pelley |
| 5,683,680 A | | 11/1997 | Santalucia et al. |
| 5,690,913 A | | 11/1997 | Hsu et al. |
| 5,709,852 A | | 1/1998 | Gopalkrishnan et al. |
| 5,756,074 A | | 5/1998 | Ascione et al. |
| 5,855,874 A | | 1/1999 | Gopalkrishnan et al. |
| 5,885,555 A | | 3/1999 | Sheehan |
| 5,919,830 A | | 7/1999 | Gopalkrishnan et al. |
| 6,121,213 A | | 9/2000 | Vergara et al. |
| 6,159,449 A | | 12/2000 | Winston et al. |
| 6,214,321 B1 | | 4/2001 | Lee et al. |
| 6,248,310 B1 | | 6/2001 | Lee et al. |
| 6,521,215 B2 | | 2/2003 | Okay |
| 6,576,227 B1 | | 6/2003 | Montgomery |
| 6,685,916 B1 | | 2/2004 | Holme et al. |
| 6,861,048 B2 | | 3/2005 | Yu et al. |
| 7,125,543 B2 | | 10/2006 | Hodosh |
| 7,182,937 B2 | | 2/2007 | Xu et al. |
| 7,189,385 B2 | | 3/2007 | Montgomery |
| 7,387,774 B2 | | 6/2008 | Faller et al. |
| 2006/0002865 A1 | * | 1/2006 | Buelo .............................. 424/53 |
| 2007/0071696 A1 | | 3/2007 | Wang et al. |

* cited by examiner

*Primary Examiner* — Walter Webb
(74) *Attorney, Agent, or Firm* — Fishman & Associates, LLC

(57) ABSTRACT

The present invention is directed towards anhydrous, single-part multi-purposed dentifrice and methods for removing plaque, whitening and remineralizing teeth.

8 Claims, No Drawings

MULTI-PURPOSED DENTIFRICE

CROSS-REFERENCE TO RELATED APPLICATION

This application is related to U.S. Provisional Patent Application Ser. No. 61/389,400 filed Oct. 4, 2010 and takes priority therefrom.

FIELD OF THE INVENTION

The present invention relates to multi-purposed dentifrice products.

BACKGROUND OF THE INVENTION

Dental caries, i.e., tooth decay, is a leading cause of tooth damage in humans. Dental caries begins with lesions of so-called "white spots", which are demineralized areas below the surface of intact dental enamel. Such subsurface lesions are formed before a cavity is detectable. If unchecked, surface enamel above a subsurface lesion eventually collapses, leading to cavitations and subsequent loss of tooth structure.

The primary component of the enamel and dentin in teeth is calcium phosphate in the form of calcium hydroxyapatite. This material is highly insoluble at normal oral pHs. However, calcium phosphate salts are more soluble in acidic media, and they are subjected to acids produced from the glycolysis of sugars by the action of various oral bacteria. Therefore, the acids cause carious lesions that form in teeth.

Although it is desirable to prevent caries from spreading, it is also desirable to restore the carious tooth to its original state. Restoration of a carious tooth to its original state involves the process of remineralization. The object of remineralization is to deposit hydroxyapatite in the carious lesion such that the dental enamel incorporates the hydroxyapatite into its structure at the point of lesion. Thus, remineralization not only prevents further tooth decay but also restores the tooth to its original state.

Saliva is supersaturated with respect to calcium and phosphate ions. Saliva therefore helps protect teeth against demineralization and can slowly remineralize teeth that have become demineralized by acids. It is also well known that the presence of fluoride ions can enhance the natural remineralization process and this is one of the accepted mechanisms by which fluoride toothpastes and rinses protect against caries. However, the modest levels of calcium and phosphate in saliva limit the efficacy of fluoride containing toothpastes and rinses to remineralize teeth. Therefore, it is highly desirable to increase the available concentration of calcium and phosphate ions in the oral cavity to speed up the remineralization process. To do so, one must taking into account of calcium phosphate's low solubility at the pH of saliva, and that calcium ions must be prevented from reacting with the phosphate ions or fluoride ions until immediately before use, so that the ions would not precipitate prematurely before reach oral cavity.

A variety of methods and compositions have been described in the prior art to attempt to cure the deminineralization problem. Examples are U.S. Pat. Nos. 5,037,639; 5,268,167; 5,437,857; 5,427,768; and 5,460,803 (all to Tung), teach the use of amorphous calcium compounds such as amorphous calcium phosphate (ACP), amorphous calcium phosphate fluoride (ACPF) and amorphous calcium carbonate phosphate (ACCP) for use in remineralizing teeth. These amorphous compounds or solutions which form the amorphous compounds when applied either onto or into dental tissue prevent and/or repair dental weaknesses such as dental caries, exposed roots and dentin sensitivity. The compounds are claimed to have high solubilities, fast formation rates and fast conversion rates (to apatite). In the Tung patents, remineralization is accomplished by bringing the amorphous compound into contact with the dental tissue. This can be done directly, i.e., putting an amorphous compound directly on the tooth, or indirectly through a carrier, i.e., incorporating the amorphous compound in a carrier such as a gel, a chewing gum, or a toothpaste and applying the carrier to the dental tissue. Once contact is established with the tooth, the amorphous calcium phosphate compounds will recrystallize to the less soluble apatite form in the lesion and reform the tooth. However, under conditions where amorphous calcium phosphate compounds are stable, the quantity of calcium and phosphate released is relatively low and, therefore, remineralization is slower than desirable.

The aforementioned patents to Tung teach the use of two-part solutions wherein a first part contains phosphate salt(s) and a second part contains calcium salts(s), wherein either the first part or the second part further contains carbonate salt(s). In addition, the Tung patents teach solutions formed by dissolving in water a solid powder containing calcium salt(s). These solutions are salt(s) and carbonate salt(s). These solutions are then applied to dental tissue. The Tung patents further teach the use of non-carbonated solid powders containing mixtures of calcium salts and phosphate salts which can be applied directly to the tooth or dispersed in gel, chewing gum, or other non-aqueous medium such as toothpaste which is placed in contact with the tooth. The patents teach that these powders are easily dissolved in saliva and then reprecipitated as an amorphous calcium phosphate compound. However, the Tung patents do not disclose the pHs of aqueous solutions formed from the non-carbonated solid powders.

Another example is U.S. Pat. No. 5,571,502 to Winston et al. is directed to one-part, non-aqueous products and methods of using same to remineralize subsurface lesions, wherein the products contain at least one water-soluble calcium salt; at least one water-soluble phosphate salt; either a stabilizer or a hydrophilic, non-aqueous, water-soluble vehicle; and, optionally, at least one water-soluble fluoride salt. When the components are mixed with water or saliva to form an aqueous mixed solution, the solution has a pH of from about 4.5 to about 10.0.

Another example is U.S. Pat. No. 6,159,449 to Winston et al., is directed to two-parts, simultaneously releasable dentifrice. Such dentifrice compositions are capable of providing remineralization of subsurface lesions and/or mineralization of exposed dentinal tubules.

Another example is U.S. Pat. No. 6,214,321 to Lee et al. discloses a two-parts dentifrice that includes one part made of water soluble calcium phosphate salt having a pH less than 7, and a second part containing an alkaline material and a fluoride ion source to achieve a pH greater than 7.5. The two parts are stored separated and simultaneously released to generate hydroxyapatite depositing on dental enamel.

Besides dental caries, another major teeth problem facing the consumers is dental plaque build-up. Dental plaque is essentially a colorless biofilm that develops naturally on the teeth by colonizing bacteria attaching itself to a smooth surface (of a tooth). Dental plaque is soft enough to come off if scraped with a fingernail. However, If not removed, the plaque starts to harden and calcified within 48 hours, and in about 10 days the plaque becomes dental calculus (tartar), rock-hard and difficult to remove.

As the mature calculus develops, it becomes visibly white or yellowish in color unless stained or discolored by some extraneous agent. In addition to being unsightly and undesirable from an aesthetic standpoint, the mature calculus deposits can be constant sources of irritation of the gingival, causing gingivitis, which if left untreated, results in periodontitis. Generally periodontitis cannot be treated by superficial use of chemotherapeutic agents, and the intervention of a dentist is required and surgery is often necessary.

A variety of methods and compositions have been described in the prior art to attempt to remove or prevent plaque and/or tartar. One example is U.S. Pat. No. 5,455,024 to Winston et al. discloses dentifrices comprised of sodium bicarbonate, zinc oxide, and an anti-caries agent to inhibit the formation of plaque Another example is U.S. Pat. No. 6,248,310 to Lee et al. discloses a two-parts dentifrice that includes one part made of water soluble calcium phosphate salt having a pH less than 7, and a second part containing an alkaline material and a fluoride ion source to achieve a pH greater than 7.5. The two parts are stored separated and simultaneously released to generate a system for inhibiting tartar around the teeth.

While periodontitis, gingivitis, and tooth decay have longed vexed the human population, ill appearance of teeth due to stains are equally undesirable. Indeed, many individuals desire a "bright" smile and white teeth, and consider dull and stained teeth cosmetically unattractive. Unfortunately, without preventive or remedial measures, stained teeth are almost inevitable due to the absorbent nature of dental material.

Stains on teeth can be of the extrinsic or intrinsic type. The types of attractive forces involved in extrinsic dental stains include electrostatic and van der Waal forces, hydration forces, hydrophobic interactions, dipole-dipole moment forces, and hydrogen bonds. The strength of adhesion for chromogens and pre-chromogens are not well understood. A method of classification was attempted to further describe dental stains which involves three categories (Nathoo SA. The chemistry and mechanisms of extrinsic and intrinsic discoloration. *J Am Dent Assoc* 1997 April; 128 Suppl: 6S-10S).

In category 1 stains, the color of the discoloration is the same as the color of the material (chromogen) that causes the stain. The substances of tea, coffee and wine contain tannins and are composed of polyphenols such as catechins and leucoanthocyanins. These materials generate color due to the presence of conjugated double bonds and are thought to interact with the tooth surface via an ion exchange mechanism. Also included in the mechanism of adherence of the chromogen to the tooth is the salivary pellicle, a protein structure adhering to enamel via calcium bridges.

In category 2 stains, pigmented materials bind to the pellicle or tooth and subsequently change color. An example of this would be the cervical yellow stain turning brown with age. A proposed mechanism for this change is through the further accumulation or chemical modification of pellicle proteins (denaturation by acids or detergents). Intensification may occur via a metal bridging mechanism. Category 2 stains are considered to be more difficult to remove than category 1 stains.

In category 3 stains, the binding of a colorless material to teeth can undergo chemical reactions or transformations. The colorless material is termed a pre-chromogen. Examples of this type of staining are the induction of chlorhexidene stain, browning of foods high in carbohydrates and sugars via a rearrangement of the carbohydrates and amino acids, termed the Maillard or non-enzymatic browning reaction, and staining from stannous fluoride.

Thus, extrinsic stains result from chromogens binding either to enamel or probably more so to pellicle. The removal of a pellicle layer via a bleaching system will present a whiter tooth. The pellicle is a natural occurring biolayer and will re-establish itself if removed. It will do so with minimal chromogen build-up.

Intrinsic stains include phenomena occurring both before and after eruption of the tooth from the alveolar bone into the oral cavity. Pre-eruptive phenomena include endemic fluorosis, tetracycline staining, dentinogenesis imperfecta, and amelogenesis imperfecta. Post-eruptive phenomena include pulpal hemorrhaging, and deposition of secondary dentin or metals in a tooth from an amalgam restoration.

Everyday activities such as smoking or other oral use of tobacco products, and eating, chewing or drinking certain foods and beverages (in particular coffee, tea and red wine), cause undesirable staining of surfaces of teeth. Staining can also result from microbial activity, including that associated with dental plaque.

The chromogens or color causing substances in these materials become part of the pellicle layer and can permeate the enamel layer. Even with regular brushing and flossing, years of chromogen accumulation can impart noticeable tooth discoloration.

There are a variety of compositions described in the art for preventing or treating the discoloration of teeth. In particular, to combat staining and brighten or restore the natural enamel color, a variety of products containing bleaching materials are commercially available for professional and consumer use. The materials most commonly used in teeth whitening today are peroxides. Such peroxides include hydrogen peroxide, carbamide peroxide, sodium perborate, and sodium percarbonate.

When these peroxides are in appropriate contact with teeth they will usually oxidize the majority of stains, rendering the teeth whiter.

Current home whitening treatment methods include abrasive toothpastes, toothpastes that produce oxides, whitening gels for use with a dental tray and whitening strips.

The effectiveness of such techniques depends on a variety of factors including the type and intensity of the stain, the type of bleaching agent, contact time of the bleaching agent on the teeth, the amount of available bleaching active in the composition, the ability of the bleaching agent to penetrate the tooth enamel, and consumer compliance.

A variety of methods and compositions have been described in the prior art for whitening teeth. One example is U.S. Pat. No. 4,891,211 to Winston discloses a hydrogen peroxide-releasing toothpaste comprising sodium bicarbonate and sodium percarbonate in a polyethylene glycol base for removing stains and odor.

Another example is U.S. Pat. No. 6,521,215 to Okay discloses a dentifrice composition for whitening and remineralizing teeth, wherein the three key components are a whitening agent, a protease enzyme, and a remineralizing agent.

Another example is U.S. Application Number 2007/0071696 to Wang et al. discloses a dual phase whitening oral care composition. The composition includes a first phase that contains a whitening agent in a substantially anhydrous and orally acceptable carrier and a second phase that contains an abrasive and an anti-calculus agent in an orally acceptable carrier. The first phase and the second phase are maintained separately from each other until dispensed.

Although consumers recognize the need to maintain healthy teeth, and have used various dentifrice products on the markets for this purpose, it must be noted that majority of the consumers preferred flavored dentifrices, in particular those that provide a "refreshing" taste upon usage. Refreshing flavors such as wintergreen are known to degrade in liquid (aqueous and non-aqueous) alkaline environments. For non-liquid formulation, wet granulations often supply sufficient water to initiate the degradation process even though the ultimate product (pressed tablet, mint, or candy) appears dry. Meanwhile, other components have sufficient trapped water within their crystal structure which can be released on compression and initiate the degradation. Still other components are hygroscopic to a sufficient degree such that moisture is picked up from the ambient environment in sufficient amounts to initiate the degradation process.

Furthermore, significant wintergreen degradation is observed when the bicarbonate dentifrices are flavored with wintergreen. Bicarbonate containing dentifrice formulations are often prepared with various standard humectants such as propylene glycol, glycerin, and polyethylene glycol. Where water is present, the degradation is more pronounced than when water is absent, but even in the absence of water, wintergreen degradation is still significant with these humectants.

A variety of methods and compositions have been described in the prior art to incorporate flavors in alkaline dentifrices. One example is U.S. Pat. No. 5,709,852 to Gopalkrishnan et al., disclosing a stable non-aqueous carrier for personal care product containing flavor and bicarbonates, comprising about 80-98% by weight of a non-ionic liquid triblock EO/PO/EO copolymer of MW=1000-5000, and about 2-20% by weight of a non-ionic solid triblock EO/PO/EO copolymer of MW=4000-16,000.

However, none of the above products or references disclosing whitening and/or reminerialization addresses the issue of removing plaque build-up. Moreover, none of the references disclosing remineralization or removal/prevent of plaque teaches whitening teeth. Furthermore, some of the mentioned references teach that of a two-parts dentifrice, and none address the issue of flavor degradation in alkaline dentifrice. Given the tedious task of teeth maintenance, there is a need for developing a flavored single-part and multi-purposed dentifrice, such that it requires only a single application to achieve the functions of teeth whitening, teeth remineralization, and prevention or removal of plaque.

SUMMARY OF THE INVENTION

A multi-purposed, single-part dentifrice comprising a remineralization component, a teeth whitening component, and a plaque inhibiting component.

DETAILED DESCRIPTION OF THE INVENTION

A multi-purposed, single-part dentifrice comprising a) a remineralization component comprising at least one water-soluble calcium salt, at least one water-soluble phosphate salt, and, optionally, at least one water-soluble fluoride compound yielding fluoride ions; b) a teeth whitening component comprising solid or bound whitening agents which are substantially anhydrous oxygen generating compounds; c) and a plaque inhibiting component comprising at least one alkaline metal bicarbonate; and d) a substantially anhydrous and orally acceptable carrier.

The dentifrices are substantially anhydrous or non-aqueous. "Non-aqueous dentifrice" is defined as dentifrice that does not include water in such an amount that it will adversely affect the stability required by the remineralization composition of the invention, i.e., the components of the dentifrice does not contain significant quantities of free water. However, it may contain salts with water of hydration. Preferably, the dentifrice includes either no water or only traces of water.

The Dentifrice can be in the form of a mouthwash, powder, toothpaste or gel, booster to another existing dentifrice, troche, chewing gum, lozenge and the like.

Remineralizing Component

The reminerializing component contains at least one water-soluble or partially water-soluble calcium compound and at least one water-soluble inorganic phosphate compound, and optionally, at least one water-soluble fluorine compound. The ingredients are formulated into a single-part component, such that the ingredients do not react with one another to cause premature precipitation of calcium phosphate, until introduced into the oral cavity.

Suitable water-soluble or partially water-soluble calcium compounds are, for example, calcium chloride, calcium bromide, calcium sulfate, calcium nitrate, calcium acetate, calcium gluconate, calcium benzoate, calcium glycerophosphate, calcium formate, calcium fumarate, calcium lactate, calcium butyrate and calcium isobutyrate, calcium malate, calcium maleate, calcium propionate, calcium valerate or mixtures of water-soluble calcium compounds. The calcium compound is considered to be water-soluble when at least 0.25 gram thereof dissolves in 100 ml of $H_2O$ at 20° C. In the compositions of the invention for the remineralization of human dental enamel, at least about 100 ppm of calcium ions should be present; the upper limit is about 35,000 ppm of calcium ions.

As used herein, the term "partially water-soluble" with respect to the calcium salt component refers to a calcium salt having a solubility which is greater than that of dicalcium phosphate dihydrate in an aqueous solution having a pH of about 7.0 and a temperature of about 25° C. but which is less than that solubility which would release more than about 1400 ppm of calcium cations in such aqueous solution. In an aqueous solution having a pH of about 7.0 at a temperature of about 25° C., dicalcium phosphate dihydrate generally releases about 40 ppm of calcium cations. Thus, the calcium salt used in the present invention generally has a solubility such that the salt is capable of releasing more than about 40 ppm but no more than about 1400 ppm of calcium cations in an aqueous solution having a pH of about 7.0 at a temperature of about 25° C. Preferably, the calcium salt(s) used in this invention has a solubility in such aqueous solution such that the salt(s) releases from about 100 ppm to no more than about 1400 ppm of calcium cations. Calcium sulfate is preferred.

The term "water-soluble" as used herein with respect to the phosphate, fluoride and divalent metal salts suitable for use in the present invention refers to a solubility such that the salts are each capable of releasing at least about 1400 ppm of ions into an aqueous solution having a temperature of about 25° C. and a pH of about 7.0.

Suitable water-soluble inorganic phosphates within the scope of the present invention are, for example, alkali salts and ammonium salts of orthophosphoric acid, such as potassium, sodium or ammonium orthophosphate, monopotassium phosphate, dipotassium phosphate, tripotassium phosphate, monosodium phosphate, disodium phosphate and trisodium phosphate. Dipotassium phosphate is preferred. The concentration of the phosphate ions is preferably about 100 ppm to 40,000 ppm, and its solubility in water is defined as in the case of the calcium compounds.

If desired, water-soluble salts yielding both calcium and phosphate ions, such as monobasic-calcium orthophosphate, may be employed. The compositions of the invention for the remineralization or prevention of demineralization of human teeth preferably also contain water-soluble fluoride compounds, the caries-prophylactic activity of which has for a long time been considered to be established.

Suitable fluoride compounds are the alkali fluorides such as sodium, potassium, lithium or ammonium fluoride, tin fluoride, indium fluoride, zirconium fluoride, copper fluoride, nickel fluoride, palladium fluoride, fluorozirconates such as sodium, potassium or ammonium fluorozirconate or tin fluorozirconate, fluorosilicates, fluoroborates, fluorostannites. Organic fluorides, such as the known amine fluorides are also useful in the compositions of the invention.

Water-soluble alkali metal monofluorophosphates such as sodium monofluorophosphate, lithium monofluorophosphate and potassium monofluorophosphate, preferably, sodium monofluorophosphate may be employed. In addition other water-soluble monofluorophosphate salts may be employed including ammonium monofluorophosphate aluminum monofluorophosphate, and the like.

In a preferred embodiment of the present invention, the stable, one-part, non-aqueous remineralizing component contains about 0.05 wt. % to 15 wt. %, preferably about 0.10 wt. % to 10 wt. % of calcium salt yielding calcium ions, from about 0.05 wt. % to 15 wt. %, preferably about 0.10 wt. % to 10 wt. %, of a water-soluble phosphate salt yielding phosphate ions and from about 0.01 wt. % to 5.0 wt. %, preferably from about 0.02 wt. % to 2.0 wt. %, of a soluble fluoride salt yielding fluoride ions, wherein the salts are contacted with water or saliva the pH is between about 4.5 and 10.0, preferably between about 5.0 and 7.0.

Alternatively, the molar ratio of calcium and phosphate ions in the mixture is from about 0.01 to up to 100 to 1, preferably from about 0.2 to 1 up to 5 to 1, and most preferably between from about 1 to 1 and from about 1.67 to 1.

The pH of the remineralization component may be adjusted to the pH desired by methods well known in the art. The pH may be controlled by the addition of any acid which is safe for use in the oral cavity and which yields the desired pH at the amount employed. Examples of suitable acids are acetic acid, phosphoric acid, hydrochloric acid, citric acid and malic acid; by the addition of a base, for example, sodium hydroxide; or buffered, for example with sodium citrate benzoate, carbonate, or bicarbonate, disodium hydrogen phosphate, sodium dihydrogen phosphate, etc. Preferably the remineralizing salts employed can be selected to obtain the desired pH. Usually a combination of monobasic, dibasic and/or tribasic alkali metal phosphate salt is selected to provide the target pH.

Whitening Component:

The whitening component for use in the invention includes at least one solid whitening agent and/or bound whitening agent, which is a substantially anhydrous oxygen-generating compound. Solid whitening agents useful herein include peroxides, metal chlorites, persulfates, and combinations thereof. Exemplary peroxide phases include hydroperoxides, such as hydrogen peroxide, peroxides of alkali and alkaline earth metals, organic peroxy compounds, peroxy acids, pharmaceutically-acceptable salts thereof, and mixtures thereof. Other exemplary include peroxides of alkali and alkaline earth metals, organic peroxy compounds, peroxy acids and their salts, and as inorganic peroxy acid salts. Preferred whitening agents are sodium perborate, calcium peroxide, urea peroxide, sodium percarbonate, and mixtures thereof. Suitable metal chlorites include calcium chlorite, barium chlorite, magnesium chlorite, lithium chlorite, sodium chlorite, and potassium chlorite. The whitening agent may be preferably bound, unbound, and/or solid. For example, the whitening agent may be bound to a polymer such as PVP (poly(N-vinylpyrrolidone). Suitable PVP complexes are disclosed, for example, in U.S. Pat. Nos. 3,376,110, 3,480,557 and 5,122,370.

The whitening agent is present in the amount of about 0.1 wt. % to about 20 wt. %, preferably about 0.5 wt. % to about 15 wt. %, more preferably about 1.0 wt. % to about 10 wt. % of the dentifrice.

Plaque Inhibiting Component

The plaque-inhibiting component for use in the dentifrice includes at least one alkaline metal bicarbonate. It is believed that alkaline metal bicarbonate serves as an abrasive, and upon active applications, i.e. brushing against surfaces (e.g. tooth), plaque can be effectively removed.

At least one alkaline metal bicarbonate can be used, including salts selected from sodium bicarbonate, potassium bicarbonate and lithium bicarbonate. The bicarbonate particles have a mean particle size of about 5 to 200 microns. The bicarbonate particles may be incorporated in the dentifrice in varying amounts, depending upon the desired properties of the formulation. Higher levels of alkaline metal bicarbonate, e.g., about 50%, allow it to be used as the sole abrasive. Such formulations remove plaque effectively, have a desirable low abrasivity, and provide an exceptionally clean feeling to the teeth and gums after brushing. Lower levels allow the incorporation of secondary abrasives and permit the formulation of clearer gels. At very low levels, e.g., less than about 10%, the bicarbonate still provides effective buffering in the pH 7.5 to 9.5 range and enhances the clean feeling of the teeth and gums, but to a lesser degree than when high levels are used.

Conventional abrasives or polishing materials are also useful herein as a secondary abrasive. Useful water-insoluble abrasives include sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, aluminum silicate, zirconium silicate, hydrated silica, hydrated alumina, bentonite, and/or the like.

Preferred abrasive materials that may be admixed with the alkaline metal bicarbonate include hydrated silica, silica gel, or colloidal silica and complex amorphous alkali metal aluminosilicates. When visually clear gels are employed, polishing agents of hydrated or colloidal silica, alkali metal aluminosilicate complexes, and alumina are particularly useful since they have refractive indices close to the refractive indices of the gelling agent-liquid systems (including water and/or humectant) commonly used in the gels.

Any of the secondary water-insoluble abrasives may be present in amounts of up to about 50 wt. %, preferably in amounts up to about 20 wt. %, which amount will depend upon the amount of alkaline metal bicarbonate used.

Carrier

Substantially anhydrous and orally acceptable carrier is selected from polymers and copolymers of PEG, ethylene oxide and propylene oxide.

A preferred copolymer is the copolymer disclosed in commonly assigned U.S. Pat. No. 5,885,555.

The preferred embodiment is based upon a discovery that the use of a specialized polyalkyleneglycol available from BASF under the name PLURAFLO® (poloxaflo), stabilizes and prevents degradation of flavor in the bicarbonate and percarbonate dentifrices. More specifically, the specialized polyalkyleneglycol is a synthetic copolymer of ethylene and propylene oxide, purposely arranged in both block and heteric fashion. The ethylene oxide weight percent is about 60 to about 95 wt. %, preferably about 65 to about 90 wt. %, more preferably about 70 wt. % to about 85 wt. %. Each mole of polymer has from about 25 to about 50 moles, preferably from about 28 to about 48 moles of ethylene oxide units and from about 5 to about 11 moles, preferably 7 to about 9 moles, of propylene oxide. The molecular weight is generally in the range of from about 1250 to about 3000, preferably about 1500 to about 2750, most preferably about 1750 to about 2500. In addition, the specialized polyalkyleneglycol used in the invention generally conforms to general formula I below:

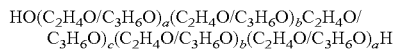

Of particular value in the present invention is poloxaflo 4370.

The poloxaflo is generally used in standard formulations (especially dentifrice formulations) as a replacement for other liquid humectants, particularly liquid polyethylene glycols, liquid pluronics, glycerin, and propylene glycol. While partial replacements of these humectants may be possible without departing from the spirit of the invention, it is preferable that all of these humectants be replaced by the poloxaflo materials set forth herein.

The poloxaflo used in the present invention is present in amounts in which other liquid humectants typically are used. In dental care products, such amounts range from less than 1 wt. % (about 0.06 for tooth powders) to in excess of about 40 wt. % for gels and pastes. Particularly preferred amounts include, about 4 wt. % to about 6 wt. %; about 12 wt. % to about 16 wt. %; and about 33 wt. % to about 36 wt. % depending on the type of formulation (powder, paste or gel).

Other suitable hydrophilic, non-aqueous vehicles for use as carriers include liquid polyethylene glycols, the humectant polyols such as glycerine, propylene glycol, dipropylene glycol and hexylene glycol. As used herein, "propylene glycol" includes 1,2-propylene glycol and 1,3-propylene glycol.

Non-ionic surfactants can also be used as the hydrophilic, non-aqueous carrier for the dentifrice, include materials such as polyoxyethylene sorbitan fatty acid esters. Polyoxyethylene fatty acid esters are also suitable for use as the vehicle in the compositions of the invention. Another suitable class of non-ionic surfactants for use as carrier in the dentifrice is polyoxyethyne fatty ethers.

Viscosity Modifier

The hydrophilic, non-aqueous, water-soluble carriers preferably provide a viscosity for the composition between about 60,000 cps. to 600,000 cps, preferably between about 150,000 cps. to about 600,000 cps. If the selected vehicle does not itself provide the desired viscosity, viscosity modifiers, and/or other vehicle agents can be included to provide such desired viscosity. In various embodiments, such viscosity modifiers are operable to inhibit settling or separation of ingredients, i.e. hydrophobic ingredients, iridescent flakes, or coloring agents.

Polyethylene glycols such as Carbowax 8000, PEG-32, PEG-4 or PEG-8 can be used to increase the viscosity of a non-aqueous system. Mineral oil, petrolatum, clays and organomodified clays, silica and mixtures thereof are also useful. Preferably, the viscosity modifier for the present invention is PEG-8 (Polyethylene Glycol 400).

The viscosity modifier is present in the amount of about 0.1 wt. % to about 20 wt. %, preferably about 0.5 wt. % to about 15 wt. %, more preferably about 1.0 wt. % to about 10 wt. % of the dentifrice.

Surfactants

Organic surfactants are useful herein to achieve increased cleaning action, to assist thorough and complete dispersion of the anti-calculus agent throughout the oral cavity, and to improve the detergent and foaming properties of the dentifrices. Anionic, nonionic or ampholytic surfactants may be used.

Examples of suitable anionic surfactants are the water-soluble salts of the higher alkyl sulfates such as sodium lauryl sulfate or other $C_8$-$C_{18}$ alkyl sulfates, water-soluble salts of higher fatty acid monoglyceride monosulfates such as the sodium salt of the monosulfate monoglyceride of hydrogenated coconut oil fatty acids, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds such as $C_{12}$-$C_{16}$ fatty acids, alkyl or acyl radicals, and the like. Examples of the last mentioned amides are N-lauryl sarcosinate and the sodium, potassium, and ethanolamine salts of N-lauroyl, N-myristoyl, or N-palmitoyl sarcosinate, which should be substantially free from soap or similar higher fatty acid materials.

Other suitable surfactants include non-ionic agents such as the condensates of sorbitan monostearate with ethylene oxide, the condensates of ethylene oxide with propylene oxide, or the condensates of propylene glycol (available under the trademark "Pluronics"). Other examples of water-soluble nonionic surfactants useful herein are the condensation products of ethylene oxide with various other compounds which are reactive therewith and have long hydrophobic chains (e.g., $C_{12}$-$C_{20}$ aliphatic chains) which condensation products ("ethoxamers") contain hydrophilic polyoxyethylene moieties, such as condensation products of polyethylene oxide with fatty acids, fatty alcohols, fatty amides, or polyhydric alcohols (e.g., sorbitain monostearate).

The various surfactants may be utilized alone or in admixture with one another. The amount of surfactant use is preferably about 0.05 wt. % to about 5 wt. %, more preferably about 0.1 wt. % to about 2.0 wt. % of the dentifrice.

Thickener

Suitable thickening agents are water-soluble salts of cellulose ethers, such as sodium carboxymethyl cellulose, hydroxy methyl cellulose, hydroxypropyl cellulose, and hydroxyethyl cellulose. Natural gums such as gum karaya, gum arabic, carrageenan and gum tragacanth can also be used. Colloidal magnesium aluminum silicate, silica aerogels, silica xerogels, fumed silica such as Aerosil® 200VS, or other finely divided silica can be used as part of the thickening agent for further improved texture.

The thickener used is present in the amount of about 0.1 wt. % to about 20 wt. %, preferably about 0.5 wt. % to about 15 wt. %, more preferably about 1.0 wt. % to about 10 wt. % of the dentifrice.

Flavor

The present dentifrice may also contain flavoring agents such as oil of wintergreen (methyl salicyate), oil of peppermint, oil of spearmint, oil of sassafras, oil of clove, or a mixture thereof from a commercial source such as Optamint® 358437 available from Symrise. The flavor used in the dentifrice is in amounts up to about 2.0 wt. %, more preferably no more than about 1.2 wt. %.

When methyl salicylate is one component of a flavoring composition, it may constitute any useful proportion of the flavoring composition, which may vary over wide ranges. Many such formulations are available commercially from a number of sources within the fragrance and flavoring industry. Use of any such methyl salicylate containing flavoring composition is within the scope of the present invention.

The hallmark of the present invention is that flavor is more stable in alkaline environments when combined with the poloxaflo set forth above than in the absence of the poloxaflo when typical liquid humectants such as liquid polyethylene glycols, liquid pluronics, glycerin, and/or propylene glycol are employed. Retention of the characteristic aroma and taste of flavor over time in the formulations of the present invention can be utilized as a measure that the stabilization effect has been realized.

Other Additives

The present dentifrice may optionally contain at least one coloring agent, sweetener, flakes, binder and/or dispersants such as a polyalkyleneglycol copolymer (poloxamer) sold under the trade name Pluraflo® L1220 to help emulsifying hydrophobic ingredients in the dentifrice.

If at least one sweetener is included, the sweetener is selected from saccharin, dextrose, levulose, sodium cyclamate, and aspartame. Mixtures of sugar with a sweetener, e.g., sucralose, are also contemplated.

If flakes are included, they will be iridescent in nature and present in amount of up to about 5%, preferably less than 3%, of the weight of the dentifrice in which they are dispersed. A particularly suitable product is obtained when the iridescent flakes are mother of pearl flakes (a true nacreous secretion found on the inner surfaces of oyster shells and made up of non-toxic $CaCO_3$). These mother of pearl flakes refract light in various wave lengths across the color spectrum and their incorporation in the transparent toothpaste (e.g. in proportions in the range of about 11/2 to 3%, preferably about 2%, for example about 13/4 to 21/4%) results in a multicolored speckled effect with the clarity of the transparent gel intact, giving a beautiful sparkle. In use, when one extrudes the product from a conventional toothpaste tube onto the toothpaste, the resulting extrudate (which usually has a thickness in the range of about 4 to 8 mm) is typically clear with visible spaced light refracting sparkling dots; as the extrudate is moved, relative to the eye of the observer, different dots become visible and the apparent colors of individual dots changes. Especially good results have been obtained with mother of pearl flakes screened so that they are retained on a 100 mesh (U.S. Standard) sieve (corresponding to a particle size of about 149 microns) and pass through a 30 mesh sieve (corresponding to a particle size of about 590 microns) with the predominant portion being larger than 200 microns.

The mother of pearl flakes can be produced by grinding oyster shells and mechanically separating the mother of pearl flakes from the balance of the ground material, as by flotation. Typically, the mother of pearl flakes are flat, smooth-surfaced, less than 50 microns thick (e.g. 10-40 microns), oval-shaped in plane view, and made up of numerous thin parallel layers (e.g. of thickness well below a micron to say 2-3 microns).

Another type of iridescent flake comprises thin transparent mica flakes coated with a thin layer of titanium dioxide. One type of such flakes or platelets has a $TiO_2$ content of about 17%, an average thickness of less than 1 micron (e.g. 0.7 micron), with the longest dimension of most of the platelets being less than about 100 microns, e.g., about 15 to 40 microns, the refractive index of the mica layer being about 1.58 and the refractive index of the $TiO_2$ layer being about 2.3. When these are incorporated into the transparent toothpaste in proportion in the range of about 0.1 to 0.3%, preferably about 1/4%, the extrudate from the toothpaste tube is also sparkling, with the individual reflecting and iridescent dots being very small and close together, giving an overall opaque pearlescent effect. Still another but less desirable type of iridescent flakes comprises mica flakes carrying the coating of another material (namely BiOCl) whose refractive index is different from that of the mica. By variation in particle concentration one can produce different effects. One may also use mixtures of various types of the flakes.

It is found, surprisingly, that the presence of the iridescent flakes not only imparts a unique esthetic appearance but also gives a substantial improvement in the properties of the dentifrice such as its ability to remove stains from the teeth. Certain iridescent flakes also substantially improve the polishing capability of the dentifrice in which they are present.

Packaging

A plurality of packaging methods may be employed in order to contain or store the components and provide effective dispensing thereof into the oral cavity.

Thus, the components of a toothpaste, gel, cream, or the like, may be simultaneously dispensed from one collapsible tube preferably made of plastic, a plastic and metal laminate, etc.

The tubes of the above embodiments are usually filled from the bottom and are subsequently sealed together by conventional techniques.

Another alternative packaging arrangement comprises of a pressurized container, which is provided with a compartment and a spout. The internal pressure of the compartment is maintained by a pressurized gas, i.e., nitrogen, at the bottom of the compartment. Operation of a mechanical actuator actuates a valve, which releases the contents of the compartment through the spout causing discharge of the paste or gel components onto a brush.

The mouthwash or rinse and similar liquid embodiments are maintained in a manner similar to the pastes or gels in that during storage, each of the components are stabilized with regards to one another to prevent premature reaction. Upon dispensing, the components mix and react in the oral cavity to effect remineralization of dental enamel. The liquid components can therefore be stored in the compartment of a dispenser. The dispenser usually includes a closure system comprising for example, an inclined crown portion, a pouring spout extending upwardly from an upper surface of the crown portion and a cover for securement to the crown portion. The cover is provided with closure means, for example, depending plugs, to close the closure. The pouring spout is preferably provided with a vent opening in addition to a product orifice in the spouts. Transparent containers have proven to be the most satisfactory. Transparency aids a person's ability to accurately and controllably dispense relatively exact volumes from a dispenser. Transparent walled containers also serve as a window function for gauging the amounts of liquid remaining in the dispenser. The walls of the containers can be scribed or otherwise calibrated to assist in dispensing the correct amount of product.

Method of Use

With regard to the length of time of exposure to the teeth of the dentifrice applied to, or formed in, the oral cavity it is necessary that the period of time be great enough for whitening, plaque removal, and to allow diffusion of the ions into the demineralized subsurface. At least about ten seconds are required for the remineralization diffusion. The dentifrice is preferably applied to the teeth for from about 10 seconds to about 5 minutes. The pH of the dentifrice remains relatively constant after its introduction into the oral cavity. Calcium phosphate may precipitate at this pH, but most surprisingly while some of the precipitation may occur immediately and some small amount even before application to the teeth, sufficient calcium, phosphate and fluoride ions remain in solution to diffuse into the teeth and remineralize the demineralized dental enamel. It is believed that the ability of the dentifrice to provide ions for remineralization is greatest upon their first introduction into the oral cavity, thereafter decreasing. Meanwhile, for whitening and plaque removal can be achieved by actively applying the dentifrice onto the surface of the teeth at least once, preferably twice a day.

With toothpaste, gel, and the like, mixing is achieved on the surface to the teeth while brushing and with a liquid non-aqueous mouthwash upon introduction into the oral cavity. The essence of the present invention lies with the stable, single part product; in the mixing of the product components in the mouth; and the quick and timely application of the resulting aqueous solution which will precipitate calcium phosphate, calcium fluoride, and calcium fluoro-apatite in the subsurface enamel of the teeth. Surprisingly, the solution can have a pH of about 4.5 to 10, but preferably about 5.0 to 7 to achieve this result. At a pH below about 3, demineralization occurs rapidly. A pH below 2.5 is generally undesirable from a safety standpoint.

EXAMPLE I

A toothpaste composition was made of the following ingredients, labeled as "CCES":

| Chemical/INCI Name | Trade Name | Function | % Level |
|---|---|---|---|
| Sodium Bicarbonate | Sodium Bicarbonate Gr. 3 Low Fe | Abrasive | 50.00 |
| PEG/PPG-38/8 Copolymer | Pluraflo L4370 | Solvent | 35.35 |
| PEG/PPG-116/66 Copolymer | Pluraflo L1220 | Solvent | 3.50 |
| Calcium Sulfate | Calcium Sulfate Anhydrous | Calcium Replenisher | 3.00 |
| Silica | Aerosil 200VS | Thickener | 2.00 |
| Sodium Lauryl Sulfate | Sodium Lauryl Sulfate | Surfactant | 1.50 |
| Flavor | Optamint 358437 | Flavor | 1.40 |
| PEG-8 | PEG-8 | Viscosity Modifier/Humectant | 1.00 |
| Dipotassium Phosphate | Potassium Phoasphate Dibasic | Phosphate Replenisher | 1.00 |
| Sodium Saccharin | Sodium Saccharin | Sweetener | 0.65 |
| Sodium Carbonate Peroxide | Sodium Percarbonate | Whitening | 0.36 |
| Sodium Fluoride | Sodium Fluoride, Milled, USP | Anticaries | 0.243 |
| | | Total: | 100.00 |

The ingredients were mixed in the following orders:

1, Added Pluraflo® L4370, Pluraflo® L1220, PEG-8, and Sodium Bicarbonate into mixing vessel.
2. Mixed for 10 minutes under vacuum.
3. Added Calcium Sulfate, Fluororide, Dipotassium Phosphate, Sodium Saccharin, and Sodium Percarbonate.
4. Mixed for 5 minutes under vacuum.
5. Added Aerosil® 200VS.
6. Mixed for 45 minutes under vacuum.
7. Added Sodium Lauryl Sulfate and Flavor.
8. Mixed for 5 minutes under vacuum.
9. Discharged batch.

All Steps occurred between about 23.8° C. to 29.4° C., preferably room temperature.

EXAMPLE II

GROUP ANALYSIS SUMMARY OF CARIES INCIDENCE AND SEVERITY SCORES FOR TOTAL (FISSURE + SMOOTH) SURFACES

| Group[4] | N | "E" Lesion Scores Mean ± SE[H] | Caries Severity Scores Mean ± SE[H] |
|---|---|---|---|
| 1 | 30 | 33.00 ± 3.01 | 23.03 ± 2.62 |
| 2 | 30 | 54.83 ± 3.25 | 41.20 ± 4.52 |
| 3 | 30 | 18.37 ± 1.66 | 9.53 ± 1.48 |

| Group[4] | N | "Ds" Lesion Scores Mean ± SE[H] | "Dm" Lesion Scores Mean ± SE[H] |
|---|---|---|---|
| 1 | 30 | 18.23 ± 1.90 | 4.70 ± 0.79 |
| 2 | 30 | 31.40 ± 2.82 | 9.40 ± 1.56 |
| 3 | 30 | 8.47 ± 1.14 | 1.07 ± 0.42 |

[4]Group Identification:
1 = FDA USP standard control
2 = Placebo
3 = CCES from Example I
[H]Standard error of the mean.

It can be shown that the present invention CCES reduced the occurrence of caries in rates up to 60% better than the FDA USP standard control.

EXAMPLE III

Determination of the Incipient Lesion Enamel Fluoride Uptake from NaF Dentifrices An in vitro study was conducted to determine the effect of dentifrices on promoting fluoride uptake into incipient enamel lesions.
Procedure Sound, upper, central, bovine incisors were selected and cleaned of all adhering soft tissue. A core of enamel 3 mm in diameter was prepared from each tooth by cutting perpendicular to the labial surface with a hollow-core diamond drill bit. This was performed under water to prevent overheating of the specimens. Each specimen was embedded in the end of a plexiglass rod (¼" diameter×2" long) using methylmethacrylate. The excess acrylic was cut away exposing the enamel surface. The enamel specimens were polished with a 600 grit wet/dry paper and then with micro-fine Gamma Alumina. The resulting specimen was a 3 mm disk of enamel with all but the exposed surface covered with acrylic.

Each enamel specimen was then etched by immersion into 0.5 ml of 1M $HClO_4$ for 15 seconds. Throughout the etch period the etch solutions were continuously agitated. A sample of each solution was then buffered with TISAB to a pH of 5.2 (0.25 ml sample, 0.5 ml TISAB and 0.25 ml 1N NaOH) and the fluoride content determined by comparison to a similarly prepared standard curve (1 ml std and 1 ml TISAB). For use in depth of etch calculation, the Ca content of the etch solution was determined by taking 50 µl and analyzing for Ca by atomic absorption (0.05 ml qs to 5 ml). These data were the indigenous fluoride level of each specimen prior to treatment.

The specimens were once again ground and polished as described above. An incipient lesion was formed in each enamel specimen by immersion into a 0.1M lactic acid/0.2% Carbopol 907 solution for 24 hours at room temperature.

These specimens were then rinsed well with distilled water and stored in a humid environment until used.

The treatments were performed using supernatants of the dentifrice slurries. The slurries consisted of 1 part dentifrice (or powder) and 3 parts (9 g:27 ml, w/w) distilled water. Each slurry was mixed well and then centrifuged for 10 minutes at ~10,000 rpm. The specimens were then immersed into 25 ml of their assigned supernatant with constant stirring (350 rpm) for 30 minutes. Following treatment, the specimens were rinsed with distilled water. One layer of enamel was then removed from each specimen and analyzed for fluoride and calcium as outlined above (i.e., 15 second etch). The pretreatment fluoride (indigenous) level of each specimen was then subtracted from the post treatment value to determine the change in enamel fluoride due to the test treatment.

Statistical Analyses

Statistical analyses were performed with a one-way analysis of variance model using Sigma Stat software (3.1). Since significant differences were indicated, the individual means were analyzed by the Student Newman-Keuls (SNK) test.

Results

| Change in Incipient Lesion Enamel Fluoride Content Enamel Fluoride Concentration (ppm) | | | |
|---|---|---|---|
| Dentifrice | Pre Treatment | Post Treatment | Increase |
| FDA USP Standard control | 34 ± 2 ** | 1315 ± 30 | 1281 ± 29 |
| Placebo | 37 ± 3 ** | 44 ± 3 | 7 ± 5 |
| CCES from Example I | 42 ± 3 ** | 1710 ± 49 | 1668 ± 50 |

** Values do not differ significantly (p > 0.05) as determined by Newman-Keuls analysis.

It can be shown that placebo was significantly less effective in promoting enamel fluoride uptake than the other two dentifrices tested. In fact, Placebo did not promote any significant degree of enamel fluoride uptake. The other two dentifrices (FDA USP Standard Control and CCES) were both significantly more effective than Placebo. They were also different from each other, with CCES being significantly more effective than FDA USP Standard (about a 30% increase) with regard to promoting enamel fluoride uptake.

What is claimed is:

1. A substantially anhydrous single-part dentifrice consisting essentially of:

a) re-mineralization component comprising a soluble or partially soluble calcium salt, and at least one water-soluble phosphate salt selected from the group consisting of potassium, sodium or ammonium orthophosphate, monopotassium phosphate, dipotassium phosphate, tripotassium phosphate, monosodium phosphate, disodium phosphate, trisodium phosphate, monobasic-calcium orthophosphate, and mixtures thereof;

b) a teeth whitening component comprising an oxygen generating compound;

c) at least one alkaline metal bicarbonate; and d) a substantially anhydrous and orally acceptable carrier, that is an ethylene oxide/propylene oxide block copolymer of the formula:

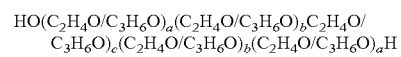

wherein per mole of such copolymer there are a total of about 25 to about 50 moles of ethylene oxide units and about 5 to about 11 moles of propylene oxide units, and said copolymer has a molecular weight of from about 1250 to about 3000 in an amount of about 33 wt. % to 40 wt. % of said dentifrice;

e) a nonionic surfactant that is a PEG/PPG-116/66 copolymer in an amount of 0.05-5 wt. % of said dentifrice;

f) a fluoride compound;

g) a sulfonated or sulfated anionic surfactant; and h) a thickener.

2. The dentifrice of claim 1, containing up to about 50 wt. % alkaline metal bicarbonate.

3. The dentifrice of claim 1, wherein calcium salt comprises calcium sulfate.

4. The dentifrice of claim 1, wherein said oxygen generating compound comprises peroxides, metal chlorites, persulfates and combinations thereof.

5. The dentifrice of claim 4, wherein said peroxides comprise alkali metal percarbonates.

6. The dentifrice of claim 1, further including at least one surfactant.

7. The dentifrice of claim 1, further including a flavoring agent.

8. The dentifrice of claim 1, in the form of a toothpaste or gel.

* * * * *